(12) United States Patent
Yamazaki

(10) Patent No.: US 8,149,274 B2
(45) Date of Patent: Apr. 3, 2012

(54) ENDOSCOPE APPARATUS

(75) Inventor: Kenji Yamazaki, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/884,329

(22) Filed: Sep. 17, 2010

(65) Prior Publication Data

US 2011/0187842 A1 Aug. 4, 2011

Related U.S. Application Data

(63) Continuation of application No. PCT/JP2010/057070, filed on Apr. 21, 2010.

(30) Foreign Application Priority Data

May 18, 2009 (JP) .................................. 2009-120136

(51) Int. Cl.
 *H04N 7/18* (2006.01)
(52) U.S. Cl. ................................ 348/68; 348/61; 348/65
(58) Field of Classification Search .................... 348/61, 348/65, 68
 See application file for complete search history.

(56) References Cited

U.S. PATENT DOCUMENTS

| 2004/0122291 A1 | 6/2004 | Takahashi |
| 2008/0255411 A1 | 10/2008 | Kobayashi |

FOREIGN PATENT DOCUMENTS

| DE | 41 38 128 A1 | 5/1993 |
| JP | 10-262922 A | 10/1998 |
| JP | 2003-135393 | 5/2003 |
| JP | 2005-124755 | 5/2005 |
| JP | 2007-125150 | 5/2007 |
| JP | 2008-086697 | 4/2008 |
| WO | WO 03/037173 A1 | 5/2003 |

OTHER PUBLICATIONS

International Search Report dated Jul. 20, 2010.
Supplementary European Search Report dated Dec. 1, 2011 from corresponding European Patent Application Publication No. 10 77 7648.6.

*Primary Examiner* — Allen Wong
(74) *Attorney, Agent, or Firm* — Scully, Scott, Murphy & Presser, P.C.

(57) ABSTRACT

An endoscope apparatus of the present invention includes a light quantity adjusting section that adjusts outgoing light quantity from a light source section that generates light irradiating a subject, a current control section that controls a current to be applied to the light source section, an image pickup section provided with an image pickup device that picks up an image of the subject, an identification section that identifies whether or not the image pickup device is provided with a shutter function, a brightness detection section that detects brightness based on an image pickup signal from the image pickup section, a white balance acquiring section for acquiring information on white balance adjustment processing, an amount of adjustment control section that controls an amount of adjustment of the light quantity adjusting section to a predetermined amount according to a white balance information acquiring operation in the white balance acquiring section, and a control section that controls the current control section or the shutter function of the image pickup device based on the output result from the brightness detection section and the output result from the identification section.

6 Claims, 8 Drawing Sheets

US 8,149,274 B2

ENDOSCOPE APPARATUS

CROSS REFERENCE TO RELATED APPLICATION

This application is a continuation application of PCT/JP2010/057070 filed on Apr. 21, 2010 and claims benefit of Japanese Application No. 2009-120136 filed in Japan on May 18, 2009, the entire contents of which are incorporated herein by this reference.

BACKGROUND OF THE INVENTION

1. Field of the Invention

The present invention relates to an endoscope apparatus, and more particularly, to an endoscope apparatus that performs white balance adjustment based on an image pickup signal.

2. Description of the Related Art

Endoscope apparatuses having an endoscope and a light source device or the like are conventionally widely used in the medical field or the like. Endoscope apparatuses in the medical field in particular are mainly used by users for the purpose of performing treatment such as intravital inspection and observation.

In inspection and observation or the like using an endoscope apparatus in general, white balance adjustment is performed beforehand to adjust variations in sensitivity of a solid image pickup device of an endoscope, variations in optical characteristics of filters and lenses or the like in a light source device, variations in color reproduction due to variations in chromatic aberration when the endoscope and the light source device are connected. Such white balance adjustment is normally performed as adjustment corresponding to the type of illuminating light used for observation (RGB light, narrow band light, excitation light for exciting fluorescence or the like) and/or light quantity or the like. The aforementioned white balance adjustment is performed beforehand also when treatment such as inspection and observation is performed using an endoscope apparatus disclosed in, for example, Japanese Patent Application Laid-Open Publication No. 2005-124755.

On the other hand, as a light source device used for an endoscope apparatus, one provided with a diaphragm disposed on the optical path of a light source such as a lamp is widely used. Furthermore, for inspection and observation or the like using an endoscope apparatus, light adjustment control is conventionally performed which adjusts the aperture of the aforementioned diaphragm and thereby increases/decreases the light quantity of illuminating light emitted from the light source device. An endoscope apparatus disclosed in Japanese Patent Application Laid-Open Publication No. 2005-124755 also uses a light source device incorporating a diaphragm and performs light adjustment control by adjusting the aperture of the diaphragm.

SUMMARY OF THE INVENTION

An endoscope apparatus of the present invention includes a light quantity adjusting section that adjusts outgoing light quantity from a light source section that generates light irradiating a subject, a current control section that controls a current to be applied to the light source section, an image pickup section provided with an image pickup device that picks up an image of the subject, an identification section that identifies whether or not the image pickup device is provided with a shutter function, a brightness detection section that detects brightness based on an image pickup signal from the image pickup section, a white balance acquiring section for acquiring information on white balance adjustment processing, an amount of adjustment control section that controls an amount of adjustment of the light quantity adjusting section to a predetermined amount according to a white balance information acquiring operation in the white balance acquiring section, and a control section that controls the current control section or the shutter function of the image pickup device based on the output result of the brightness detection section and the output result from the identification section.

DETAILED DESCRIPTION OF THE PREFERRED EMBODIMENT

Hereinafter, an embodiment of the present invention will be described with reference to the accompanying drawings. FIG. 1 to FIG. 12 are related to an embodiment of the present invention.

Figure 1:
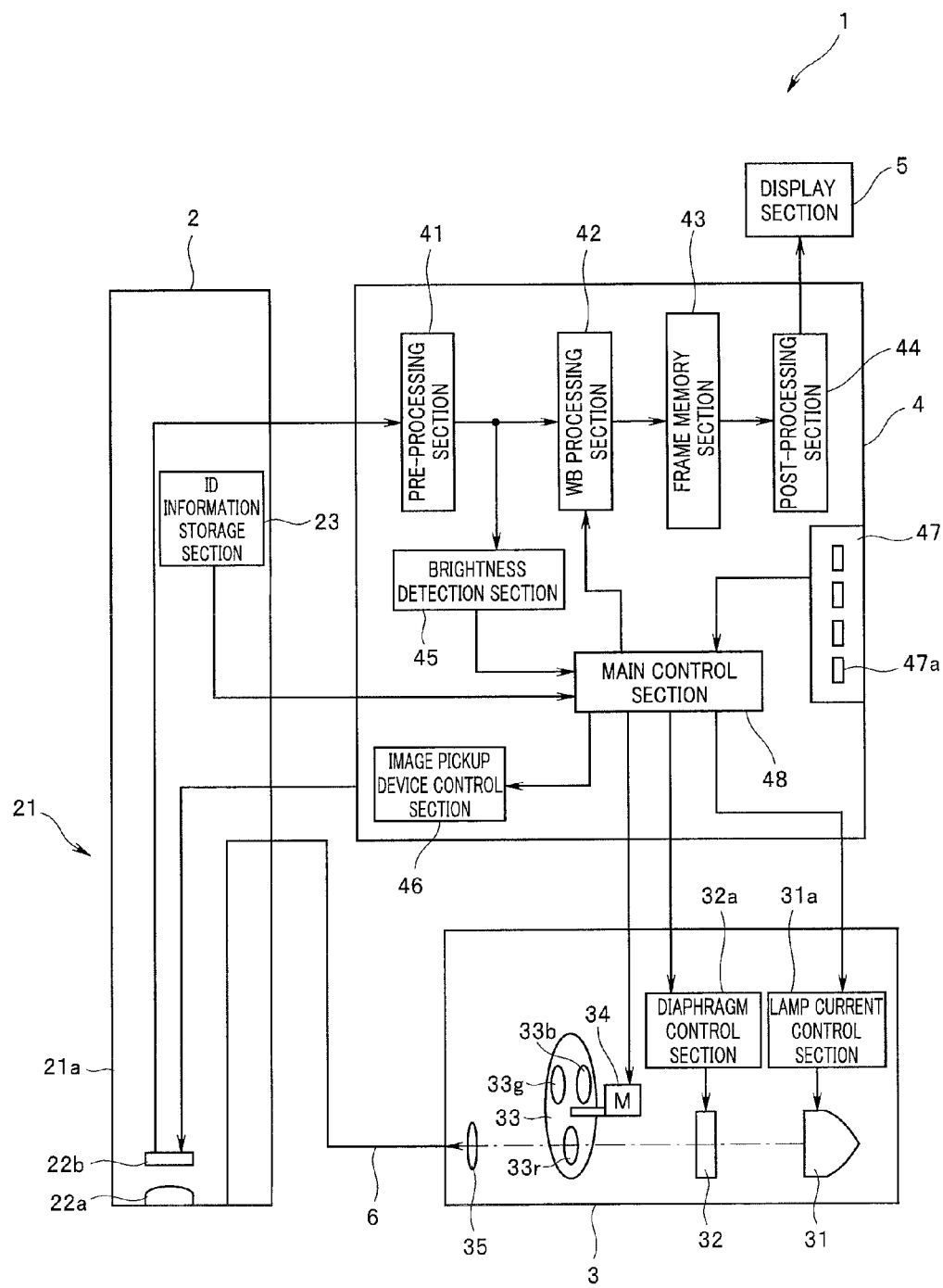
FIG. 1 is a diagram illustrating an example of a configuration of main parts of an endoscope apparatus according to an embodiment of the present invention.

As shown in FIG. 1, the endoscope apparatus 1 includes an endoscope 2 that acquires a subject image in the body cavity of a subject and outputs an image pickup signal corresponding to the subject image, a light source device 3 that supplies illuminating light to the endoscope 2, a processor 4 that converts the image pickup signal outputted from the endoscope 2 to a video signal and outputs the video signal and a display section 5 that displays a subject image corresponding to the video signal outputted from the processor 4.

The endoscope 2 has a long flexible insertion portion 21. Furthermore, a light guide 6 for transmitting illuminating light emitted from the light source device 3 to a distal end portion 21a is inserted into the insertion portion 21.

One end face (incident end face) of the light guide 6 is connected to the light source device 3. Furthermore, the other end face (outgoing end face) of the light guide 6 is disposed in the vicinity of an illumination optical system (not shown) provided in the distal end portion 21a. With such a configuration, the illuminating light emitted from the light source device 3 is emitted to the subject via the light guide 6 and an illumination optical system (not shown).

An objective optical system 22a that forms a subject image and an image pickup device 22b disposed at the image forming position of the objective optical system 22a are disposed at the distal end portion 21a of the insertion portion 21.

The image pickup device 22b picks up an image of the subject image formed by the objective optical system 22a and outputs an image pickup signal corresponding to the subject image to the processor 4. That is, the endoscope 2 of the present embodiment has the function as an image pickup section.

Furthermore, an ID information storage section 23 that stores various kinds of information including information on the presence/absence of a shutter function of the image pickup device 22b is provided inside the endoscope 2. When the endoscope 2 and the processor 4 are electrically connected, the information is read by the processor 4.

The light source device 3 is configured by including a lamp 31 as a light source that emits white color light, a lamp current control section 31a that adjusts a lamp current supplied to the lamp 31 based on the control of the processor 4, a diaphragm 32 disposed on the optical path of the lamp 31, a diaphragm control section 32a that adjusts the aperture of the diaphragm 32 based on the control of the processor 4, a revolving filter 33 provided with a plurality of filters sequentially inserted on the optical path of the lamp 31, a motor 34 that rotates the revolving filter 33 based on the control of the processor 4, and a condensing optical system 35 that condenses light that has passed through the revolving filter 33 and supplies the light to the light guide 6.

That is, the light quantity adjusting section of the present embodiment is configured by including the diaphragm 32 and the diaphragm control section 32a. Furthermore, the current control section of the present embodiment is configured by including the lamp current control section 31a.

The revolving filter 33 is disposed at the following stage of the diaphragm 32 and configured into a disk shape whose center constitutes the axis of rotation. Furthermore, the revolving filter 33 is provided with an R filter 33r that allows red color region light (R light) to pass, a G filter 33g that allows green color region light (G light) to pass and a B filter 33b that allows blue color region light (B light) to pass arranged along the outer circumferential direction on the outer circumferential side.

According to such a configuration, the revolving filter 33 is rotated according to a drive force generated by the motor 34, the R filter 33r, the G filter 33g and the B filter 33b are sequentially inserted on the optical path of the lamp 31 and frame sequential light is supplied to the light guide 6.

The revolving filter 33 is not exclusively configured by including the R filter 33r, the G filter 33g and the B filter 33b, but may be configured by including a filter for narrow band light observation. To be more specific, the revolving filter 33 of the present embodiment may be one having a configuration in which a filter that allows narrow band light having a center wavelength in the vicinity of 400 nm to pass and a filter that allows narrow band light having a center wavelength in the vicinity of 540 nm to pass arranged along the circumferential direction.

The processor 4 is configured by including a pre-processing section 41, a WB (white balance) processing section 42, a frame memory section 43, a post-processing section 44, a brightness detection section 45, an image pickup device control section 46, an operation instruction section 47 and a main control section 48.

The pre-processing section 41 applies signal processing such as amplification, noise reduction and A/D conversion to the image pickup signal outputted from the image pickup device 22b and outputs an image signal generated through the signal processing to the WB processing section 42 and the brightness detection section 45.

The WB processing section 42 applies white balance adjustment processing to the image signal outputted from the pre-processing section 41 at timing corresponding to the control of the main control section 48. The WB processing section 42 then outputs the image signal subjected to the white balance adjustment processing to the frame memory section 43.

The frame memory section 43 stores the image signal outputted from the WB processing section 42 in one-frame units.

The post-processing section 44 reads the image signal stored in the frame memory section 43 in one-frame units, applies processing such as gamma conversion and D/A conversion or the like to the read image signal and outputs the image signal to the display section 5 as an analog video signal.

The brightness detection section 45 detects the brightness of the subject image in the image signal outputted from the pre-processing section 41 and outputs the brightness detection result to the main control section 48.

The image pickup device control section 46 controls the drive state of the image pickup device 22b as appropriate. Furthermore, when the image pickup device 22b is provided with a shutter function (electronic shutter or mechanical shutter or the like), the image pickup device control section 46 performs drive control on the image pickup device 22b based on the control of the main control section 48.

The operation instruction section 47 is configured by including an input interface for giving various instructions to the respective sections of the endoscope apparatus 1. To be more specific, the operation instruction section 47 is configured by including at least a WB (white balance) instruction switch 47a that gives instructions associated with white balance adjustment processing.

When the endoscope 2 and the processor 4 are electrically connected, the main control section 48 reads information stored in the ID information storage section 23. Furthermore, the main control section 48 performs control on the motor 34 to cause the revolving filter 33 to rotate at a constant speed.

On the other hand, upon detecting that the WB instruction switch 47a has given an instruction of performing white balance adjustment processing, the main control section 48 performs predetermined control on the lamp current control section 31a, the diaphragm control section 32a and the image pickup device control section 46 until the detection result outputted from the brightness detection section 45 falls to or below predetermined brightness. When the detection result outputted from the brightness detection section 45 falls to or below the predetermined brightness, the main control section 48 controls the WB processing section 42 so as to start white balance adjustment processing while maintaining the control state after performing the predetermined control. Details of control contents including the predetermined control will be described later.

Here, the operation of the endoscope apparatus 1 will be described.

First, after connecting the respective sections of the endoscope apparatus 1, the user turns on power to the respective sections. As a result, the main control section 48 detects that the endoscope 2 and the processor 4 are electrically connected and reads the information stored in the ID information storage section 23.

Figure 2:
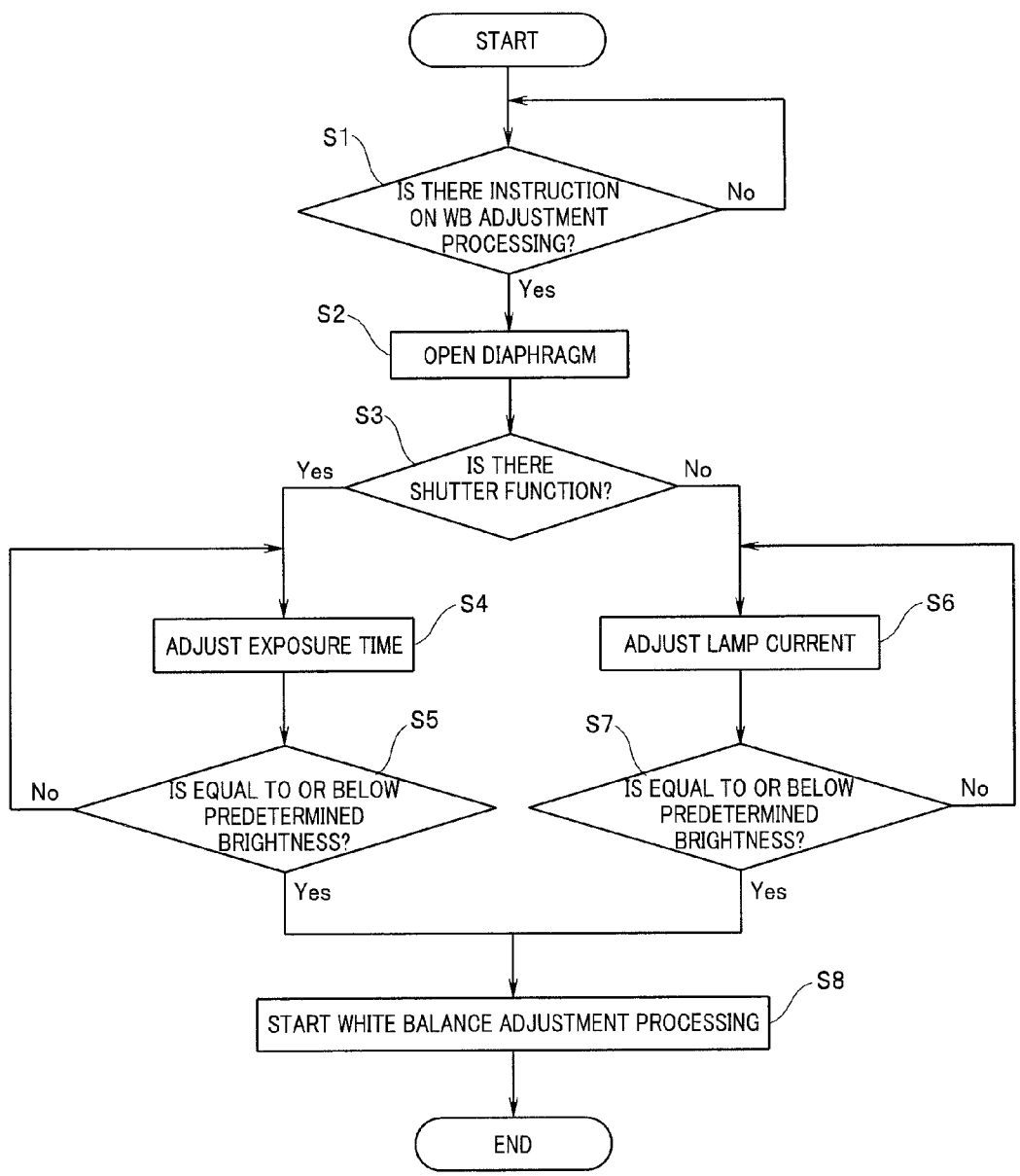
FIG. 2 is a flowchart illustrating an operation flow from around the time of an instruction for white balance adjustment processing is given until the white balance adjustment processing starts.
Figure 3:
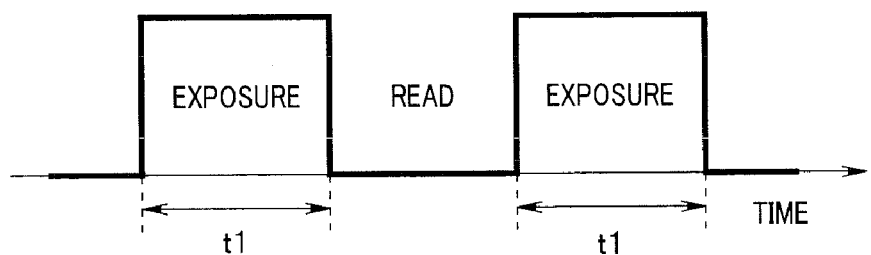
FIG. 3 is a diagram illustrating an example of an exposure period of an image pickup device.
Figure 4:
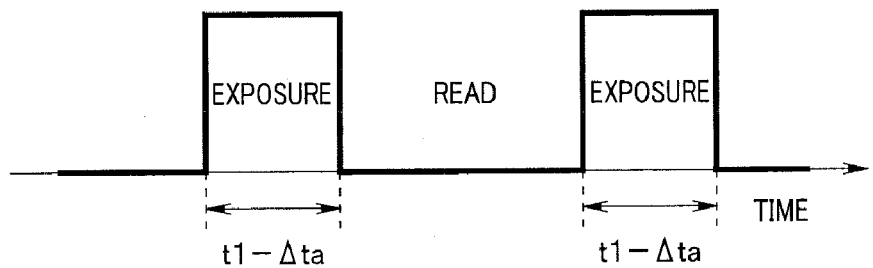
FIG. 4 is a diagram illustrating an example where the exposure period of the image pickup device is shortened from that shown in FIG. 3.
Figure 5:
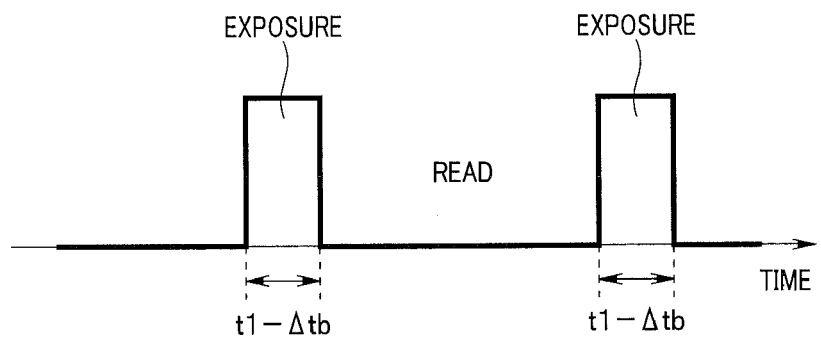
FIG. 5 is a diagram illustrating an example where the exposure period of the image pickup device is further shortened from that shown in FIG. 4.
Figure 6:
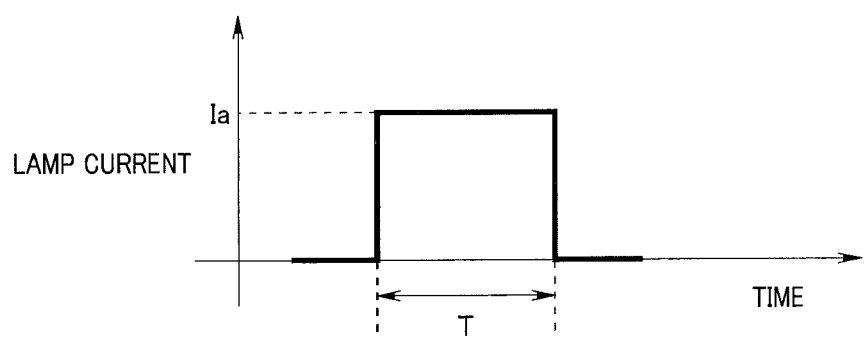
FIG. 6 is a diagram illustrating an example of a lamp current supplied to a lamp.
Figure 7:
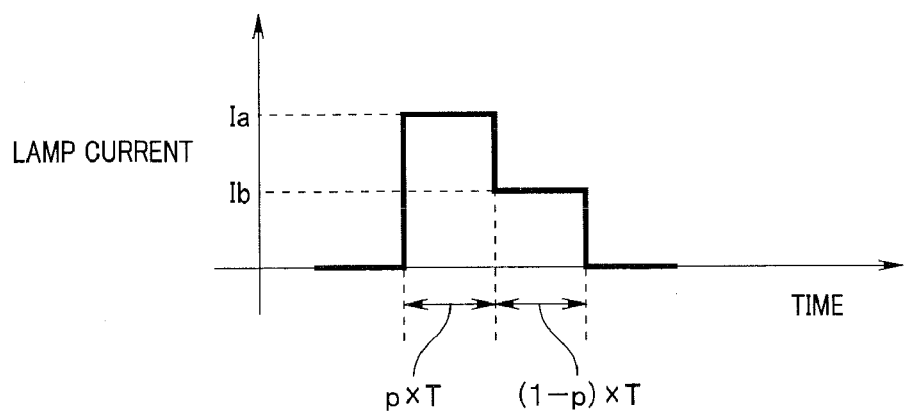
FIG. 7 is a diagram illustrating an example where the lamp current supplied to the lamp is reduced from that shown in FIG. 6.
Figure 8:
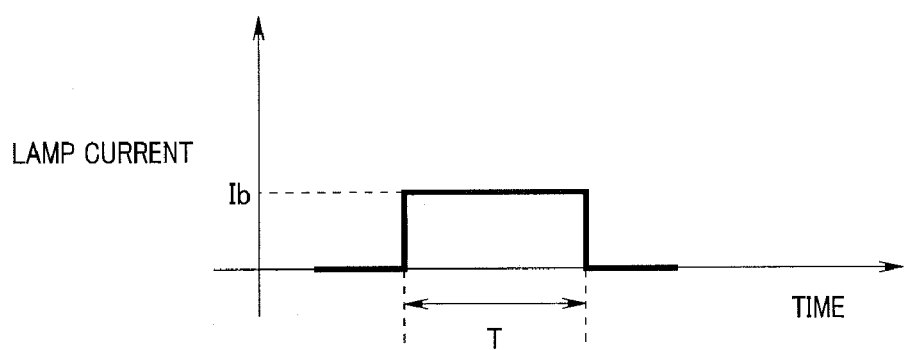
FIG. 8 is a diagram illustrating an example where the lamp current supplied to the lamp is further reduced from that shown in FIG. 7.

The main control section 48 keeps a standby state until the WB instruction switch 47a gives an instruction for white balance adjustment processing (step S1 in FIG. 2). Furthermore, upon detecting that the WB instruction switch 47a has given an instruction for white balance adjustment processing (step S1 in FIG. 2), the main control section 48 controls the diaphragm control section 32a so as to fully open the diaphragm 32 (step S2 in FIG. 2). Suppose that the diaphragm 32 is kept fully open at least for a period from the operation in step S2 in FIG. 2 being performed up to the white balance adjustment processing by the WB processing section 42 being completed.

After that, the main control section 48 having the function as an identification section identifies whether or not the image pickup device 22b is provided with the shutter function based on the information read from the ID information storage section 23 (step S3 in FIG. 2). Upon acquiring the identification result that the image pickup device 22b is provided with the shutter function, the main control section 48 moves to operations in steps S4 and S5 in FIG. 2. Furthermore, upon acquiring the identification result that the image pickup device 22b does not have a shutter function, the main control section 48 moves to operations in steps S6 and S7 in FIG. 2.

Upon acquiring the identification result that the image pickup device 22b is provided with the shutter function, the main control section 48 controls the image pickup device control section 46 so as to shorten the exposure time of the image pickup device 22b (or to delay the exposure start time of the image pickup device 22b) until the detection result outputted from the brightness detection section 45 falls to or below the predetermined brightness (steps S4 and S5 in FIG. 2).

To be more specific, when the exposure period of the image pickup device 22b is t1, and when the detection result outputted from the brightness detection section 45 is detected to have not fallen to or below the predetermined brightness, the main control section 48 controls the image pickup device control section 46 so as to shorten the exposure period of the image pickup device 22b. By operating the shutter function of the image pickup device 22b based on the control of the main control section 48, the image pickup device control section 46 shortens the exposure period of the image pickup device 22b from t1 to t1−Δta. This causes the exposure period of the image pickup device 22b to change from, for example, that shown in FIG. 3 to that shown in FIG. 4.

When the exposure period of the image pickup device 22b is t1−Δta and when the detection result outputted from the brightness detection section 45 is detected to have not fallen to or below the predetermined brightness, the main control section 48 controls the image pickup device control section 46 so as to further shorten the exposure period of the image pickup device 22b (or to further delay the exposure start time of the image pickup device 22b). The image pickup device control section 46 operates the shutter function of the image pickup device 22b based on the control of the main control section 48, and thereby shortens the exposure period of the image pickup device 22b from t1−Δta to t1−Δtb (where, Δtb>Δta). This causes the exposure period of the image pickup device 22b to change from, for example, that shown in FIG. 4 to that shown in FIG. 5.

After that, the main control section 48 performs the operations in steps S4 and S5 in FIG. 2 and upon detecting that the detection result outputted from the brightness detection section 45 finally falls to or below the predetermined brightness, the main control section 48 performs an operation in step S8 in FIG. 2 which will be described later.

On the other hand, upon acquiring the identification result that the image pickup device 22b is not provided with the shutter function, the main control section 48 controls the lamp current control section 31a so as to gradually reduce the amount of lamp current supplied to the lamp 31 until the detection result outputted from the brightness detection section 45 falls to or below the predetermined brightness (steps S6 and S7 in FIG. 2).

To be more specific, when the amount of lamp current supplied, expressed by the product of a current value Ia and an exit period T, is supplied to the lamp 31 for the exit period of light of respective colors (R light, G light and B light) and upon detecting that the detection result outputted from the brightness detection section 45 has not fallen to or below the predetermined brightness, the main control section 48 controls the lamp current control section 31a so as to reduce the amount of supply. Based on such control of the main control section 48, the lamp current control section 31a changes the amount of lamp current supplied to the lamp 31 from Ia×T to Ia×p×T+Ib×(1−P)×T (where, 0<P<1 and current value Ib<current value Ia) for the exit period of light of respective colors (R light, G light and B light). This causes the amount of lamp current supplied to the lamp 31 for the exit period of light of respective colors (R light, G light and B light) to change from that shown in FIG. 6 to that shown in FIG. 7.

Furthermore, when the amount of lamp current supplied represented by Ia×p×T+Ib×(1−p)×T is supplied to the lamp 31 for the exit period of light of respective colors (R light, G light and B light) and upon detecting that the detection result outputted from the brightness detection section 45 has not fallen to or below the predetermined brightness, the main control section 48 controls the lamp current control section 31a so as to further reduce the amount of supply. The lamp current control section 31a then changes the amount of lamp current supplied to the lamp 31 for the exit period of light of respective colors (R light, G light and B light) from Ia×p×T+Ib×(1−P)×T to Ib×T based on such control of the main control section 48. This causes the amount of lamp current supplied to the lamp 31 for the exit period of light of respective colors (R light, G light and B light) to change from that shown in FIG. 7 to that shown in FIG. 8.

After that, by performing operations in steps S6 and S7 in FIG. 2, upon detecting that the detection result outputted from the brightness detection section 45 finally has fallen to or below the predetermined brightness, the main control section 48 performs an operation in step S8 in FIG. 2 described later.

According to the present embodiment, upon acquiring the identification result that the image pickup device 22b is provided with the shutter function, the main control section 48 may also perform an operation of determining whether or not the detection result outputted from the brightness detection section 45 has fallen to or below the predetermined brightness as appropriate while performing control on both the image pickup device control section 46 and the lamp current control section 31a.

On the other hand, upon detecting that the detection result outputted from the brightness detection section 45 has fallen to or below the predetermined brightness, the main control section 48 controls the WB processing section 42 so as to start white balance adjustment processing on the image signal outputted from the pre-processing section 41 (step S8 in FIG. 2) and then ends a series of operations shown in FIG. 2.

That is, according to the above described operations, after the WB instruction switch 47a gives an instruction for white balance adjustment processing, the diaphragm 32 is fully opened and the white balance adjustment processing by the WB processing section 42 is stopped until the detection result outputted from the brightness detection section 45 falls to or below the predetermined brightness.

As described above, the endoscope apparatus 1 of the present embodiment performs white balance adjustment processing with the aperture of the diaphragm 32 fixed (fully opened), and therefore it is possible to drastically reduce variations in color reproduction after the white balance adjustment processing without substantially changing the white balance adjustment target value as a consequence. That is, the endoscope apparatus 1 of the present embodiment can suppress variations in color tone during white balance adjustment.

Figure 9:
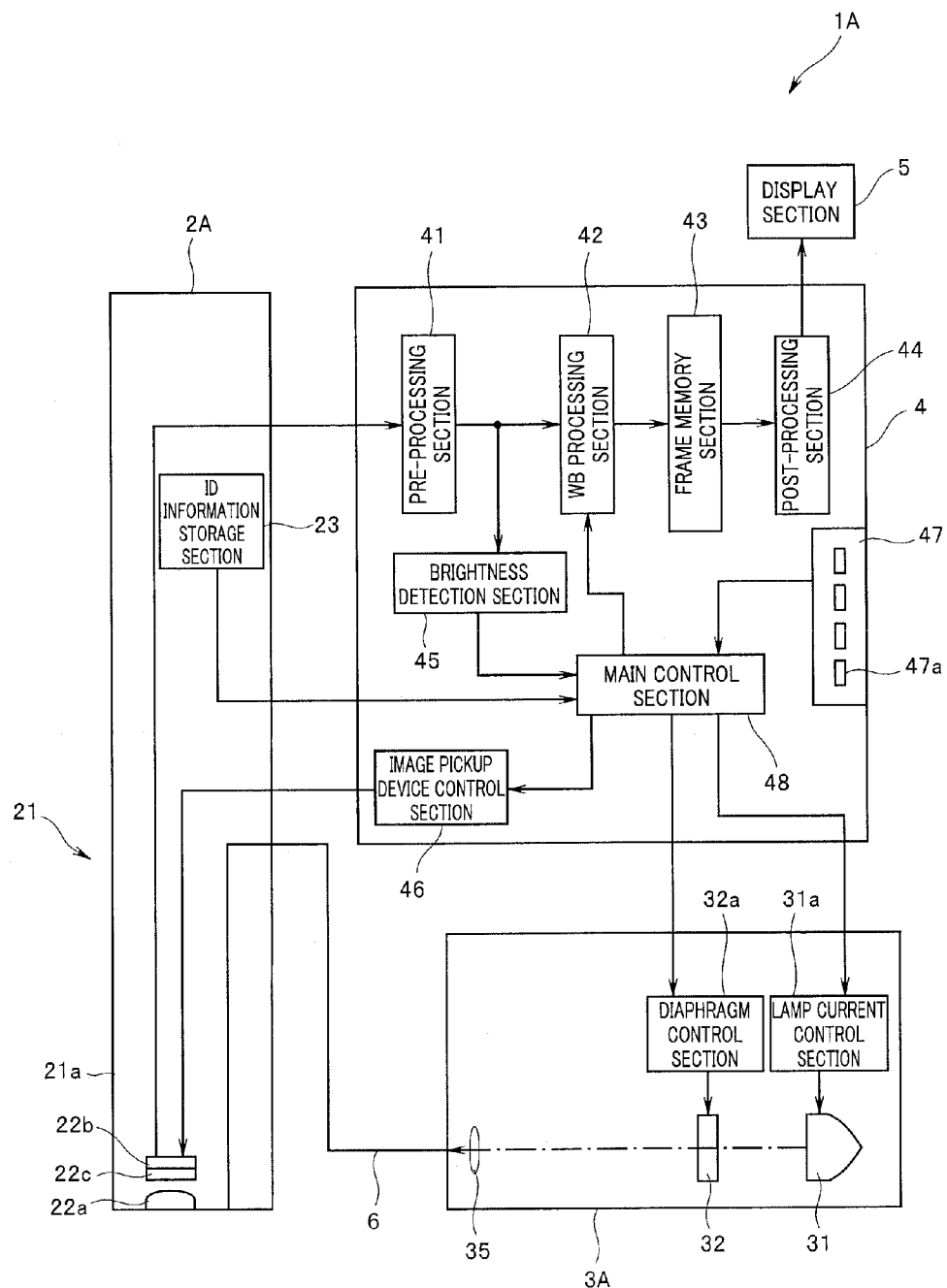
FIG. 9 is a diagram illustrating an example different from that in FIG. 1 of the configuration of main parts of the endoscope apparatus according to the embodiment of the present invention.
Figure 10:
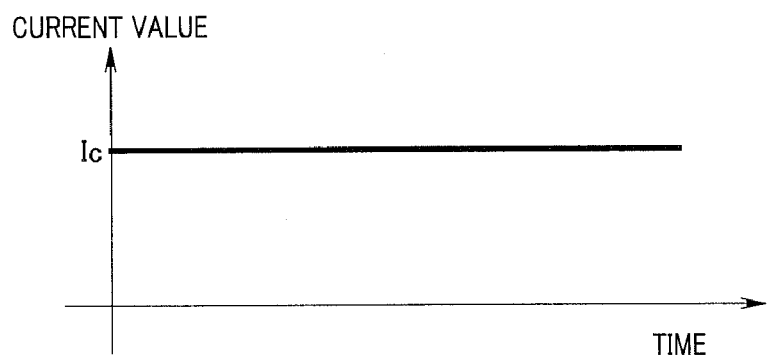
FIG. 10 is a diagram illustrating an example different from that in FIG. 6 of the lamp current supplied to the lamp.
Figure 11:
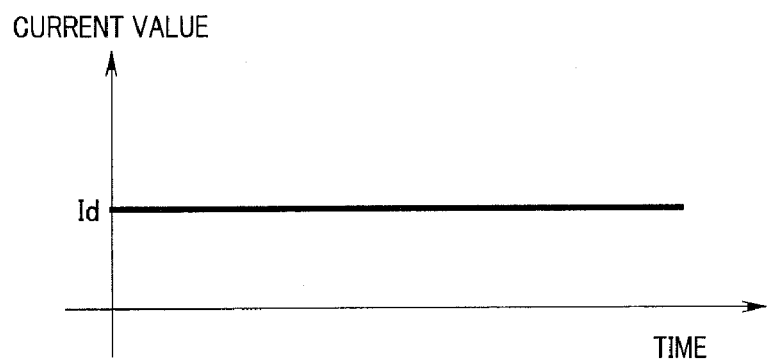
FIG. 11 is a diagram illustrating an example where the lamp current supplied to the lamp is reduced from that shown in FIG. 10.
Figure 12:
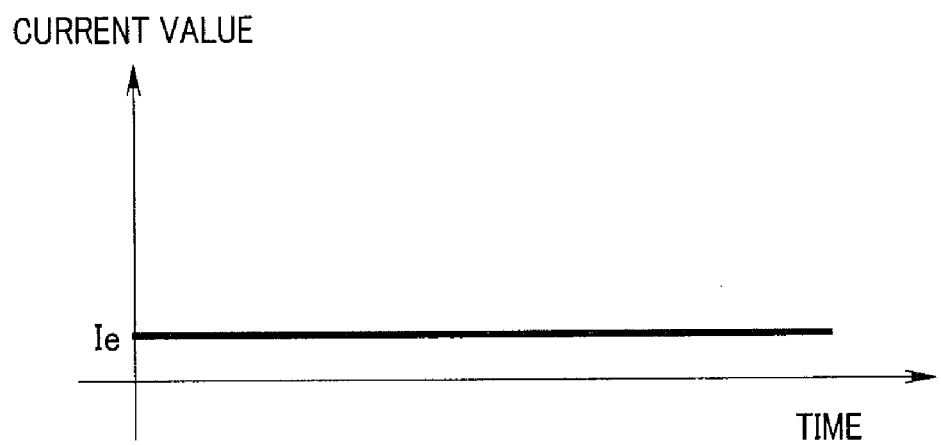
FIG. 12 is a diagram illustrating an example where the lamp current supplied to the lamp is further reduced from that shown in FIG. 11.

The present embodiment is not exclusively applied to the (frame sequential) endoscope apparatus 1 having a configuration illustrated in FIG. 1 of sequentially outputting the R light, G light and B light to the subject, but is likewise applicable to a (simultaneous type) endoscope apparatus 1A in the configuration as illustrated in FIG. 9 in which white color light is emitted to the subject.

As shown in FIG. 9, the endoscope apparatus 1A includes an endoscope 2A, a light source device 3A, a processor 4 and a display section 5.

The endoscope 2A has a configuration similar to that of the aforementioned endoscope 2 with the RGB color filter 22c disposed in front of the image pickup device 22b. That is, the endoscope 2A is provided with the function as an image pickup section.

The light source device 3A has a configuration similar to the configuration of the aforementioned light source device 3 without the revolving filter 33 and the motor 34.

The endoscope apparatus 1A having such a configuration partially changes operation contents in steps S6 and S7 of the series of operations in FIG. 2, makes operation contents in other steps agree with each other, and can thereby obtain operations substantially similar to those of the endoscope apparatus 1.

In this case, the main control section 48 controls the lamp current control section 31a so as to gradually reduce the current value of the lamp current supplied to the lamp 31 until the detection result outputted from the brightness detection section 45 falls to or below the predetermined brightness.

To be more specific, when the lamp current having a current value Ic is supplied to the lamp 31 and upon detecting that the detection result outputted from the brightness detection section 45 has not fallen to or below the predetermined brightness, the main control section 48 controls the lamp current control section 31a so as to reduce the current value of the lamp current. The lamp current control section 31a then changes the current value of the lamp current from Ic to Id (where, suppose Id<Ic) based on such control of the main control section 48. This causes the current value of the lamp current supplied to the lamp 31 to change from, for example, that shown in FIG. 10 to that shown in FIG. 11.

On the other hand, when the lamp current having a current value Id is supplied to the lamp 31 and upon detecting that the detection result outputted from the brightness detection section 45 has not fallen to or below the predetermined brightness, the main control section 48 controls the lamp current control section 31a so as to further reduce the current value of the lamp current. The lamp current control section 31a changes the current value of the lamp current from Id to Ie (where, suppose Ie<Id) based on the control of the main control section 48. This causes the current value of the lamp current supplied to the lamp 31 to change from, for example, that shown in FIG. 11 to that shown in FIG. 12.

As described so far, the endoscope apparatus 1A of the present embodiment can suppress variations in color tone during white balance adjustment as in the case of the endoscope apparatus 1.

The present embodiment is not exclusively applicable to one having a system configuration such as the endoscope apparatus 1 and the endoscope apparatus 1A, but is likewise applicable to a system or the like configured by including a capsule type endoscope, too.

Furthermore, the present invention is not limited to the aforementioned embodiment, but various changes and applications can be made without departing from the spirit and scope of the invention.

What is claimed is:

1. An endoscope apparatus comprising:
   a light quantity adjusting section that adjusts outgoing light quantity from a light source section that generates light irradiating a subject;
   a current control section that controls a current to be applied to the light source section;
   an image pickup section provided with an image pickup device that picks up an image of the subject;
   an identification section that identifies whether or not the image pickup device is provided with a shutter function;
   a brightness detection section that detects brightness based on an image pickup signal from the image pickup section;
   a white balance acquiring section for acquiring information on white balance adjustment processing;
   an amount of adjustment control section that controls an amount of adjustment of the light quantity adjusting section to a predetermined amount according to a white balance information acquiring operation in the white balance acquiring section; and
   a control section that controls the current control section or the shutter function of the image pickup device based on the output result of the brightness detection section and the output result from the identification section.

2. The endoscope apparatus according to claim 1, wherein upon acquiring an identification result that the image pickup device is provided with the shutter function from the identification section, the control section performs control so as to change an exposure time in the image pickup device while keeping an amount of adjustment of the light quantity adjusting section to the predetermined amount.

3. The endoscope apparatus according to claim 2, wherein upon acquiring an identification result that the image pickup device is not provided with the shutter function from the identification section, the control section performs control so as to change the current supplied from the current control section to the light source section while keeping the amount of adjustment of the light quantity adjusting section to the predetermined amount.

4. The endoscope apparatus according to claim 2, wherein upon acquiring an identification result that the image pickup device is provided with the shutter function from the identification section, the control section performs control so as to change the exposure time in the image pickup device and control so as to change the current supplied from the current control section to the light source section while keeping the amount of adjustment of the light quantity adjusting section to the predetermined amount.

5. The endoscope apparatus according to claim 3, wherein upon detecting that the detection result of the brightness detection section has reached a predetermined brightness as a result of changing the current supplied from the current control section to the light source section while keeping an amount of adjustment of the light quantity adjusting section to the predetermined amount, the control section causes the white balance acquiring section to start a white balance acquisition operation.

6. The endoscope apparatus according to claim 2, wherein upon detecting that the detection result of the brightness detection section has reached a predetermined brightness as a result of changing the exposure time in the image pickup device while keeping an amount of adjustment of the light quantity adjusting section to the predetermined amount, the control section causes the white balance acquiring section to start a white balance acquisition operation.

* * * * *